US009618319B2

(12) United States Patent
Nadkarni (10) Patent No.: US 9,618,319 B2
(45) Date of Patent: Apr. 11, 2017

(54) LASER SPECKLE MICRORHEOMETER FOR MEASURING MECHANICAL PROPERTIES OF BIOLOGICAL TISSUE (75) Inventor: Seemantini K. Nadkarni, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 267 days.

(21) Appl. No.: 13/985,945

(22) PCT Filed: Feb. 20, 2012

(86) PCT No.: PCT/US2012/025783
§ 371 (c)(1),
(2), (4) Date: Oct. 17, 2013

(87) PCT Pub. No.: WO2012/112977
PCT Pub. Date: Aug. 23, 2012

(65) Prior Publication Data
US 2014/0036272 A1 Feb. 6, 2014

Related U.S. Application Data (60) Provisional application No. 61/444,192, filed on Feb. 18, 2011.

(51) Int. Cl.
*G01B 9/02* (2006.01)
*G01N 21/47* (2006.01)
*A61B 5/00* (2006.01)

(52) U.S. Cl.
CPC .............. *G01B 9/02* (2013.01); *A61B 5/0059* (2013.01); *A61B 5/0066* (2013.01);
(Continued)

(58) Field of Classification Search
CPC .. G01B 9/02; G01B 9/02091; G01B 11/2441; G01B 9/02027; G01B 9/0209;
(Continued)

(56) References Cited

U.S. PATENT DOCUMENTS 7,551,293 B2 6/2009 Yelin et al.
7,597,443 B2 10/2009 Fujii et al.
(Continued)

OTHER PUBLICATIONS

"Detection of Viscoelasticity in Aggregating Dilute Protein Solutions through Dynamic Light Scattering based Optical Microrheology" to Larsson et al., Annual Transactions of the nordic rheology society, vol. 20, (2012).*
(Continued)

*Primary Examiner* — Tarifur Chowdhury
*Assistant Examiner* — Mohamed K Amara
(74) *Attorney, Agent, or Firm* — Quarles & Brady LLP (57) ABSTRACT

Volumetric distribution of a micromechanical parameter of a biological tissue, such as viscoelastic parameter or tissue stiffness, is determined, with microscopic resolution, from optical data representing light scattered by sequential layers of the tissue and, optionally, displayed to visualization. A particular layer of the tissue is defined through coherence-gating of light received at the optical detector. Coherence-gating is achieved with the use of an interferometer the sample arm of which contains the tissue, illuminated with defocused light, and an optical length of a reference arm of which is repeatedly adjusted, within a coherence length of used light, to ensure that each of the sequential optical interferograms represents light scattered only by a particular tissue layer a position of which is re-defined through the tissue via such adjustment.

33 Claims, 6 Drawing Sheets

(52) U.S. Cl.
CPC . *G01N 21/4795* (2013.01); *G01N 2203/0089* (2013.01); *G01N 2203/0094* (2013.01)

(58) Field of Classification Search
CPC ............ G01B 2290/45; G01B 9/02004; G01B 9/02057; G01B 9/04; G01B 9/02002; G01B 2290/35; G01B 11/06; G01N 21/4795; G01N 21/45; G01N 23/046; G01N 2223/419; G01N 2021/4709; G01N 21/49; G01J 9/02; G02B 26/001; G02B 26/06; G02B 21/0028; C08F 2/44; C08F 210/08; C08F 210/16; C08F 4/6495; C08F 4/6543; C08F 10/14; C08F 110/06
USPC ....... 356/450, 477, 479, 498, 497, 511, 484, 356/28.5, 4.09, 445, 35.5, 493, 32; 359/578, 370, 577, 629, 290, 291; 250/550, 201.9, 234, 227.27
See application file for complete search history.

(56) References Cited

U.S. PATENT DOCUMENTS

| | | | | |
|---|---|---|---|---|
| 8,341,100 | B2* | 12/2012 | Miller ................... | G06K 9/0014 706/15 |
| 8,568,147 | B2* | 10/2013 | Kuo ........................ | G09B 23/30 434/262 |
| 8,938,109 | B2* | 1/2015 | Treece ................... | G06T 7/0012 382/131 |
| 2003/0232895 | A1* | 12/2003 | Omidian .............. | A61K 9/0065 521/99 |
| 2006/0114467 | A1* | 6/2006 | Nicoli et al. ................... | 356/450 |
| 2008/0221814 | A1* | 9/2008 | Trainer ............................ | 702/70 |
| 2008/0262359 | A1 | 10/2008 | Tearney et al. | |
| 2010/0239672 | A1* | 9/2010 | Kemeny ................ | B82Y 30/00 424/487 |
| 2010/0284016 | A1* | 11/2010 | Teitell ..................... | G01J 3/453 356/451 |
| 2012/0105858 | A1* | 5/2012 | Popescu et al. .............. | 356/450 |
| 2012/0307035 | A1* | 12/2012 | Yaqoob et al. ................. | 348/79 |

OTHER PUBLICATIONS

Weihs et al. ("Bio-Microrheology: A Frontier in Microrheology", BioPhysical Journal vol. 91 (2006) pp. 4296-4305.*
http://www.thefreedictionary.com/dynamics.*
Abu-Yousif, et al., PuraMatrix Encapsulation of Cancer Cells, Journal of Visualized Experiments, 2009, 34, 3 pages.
Butt, et al., Force Measurements with the Atomic Force Microscope: Technique, Interpretation and Applications, Surface Science Reports, 2005, 59:1-152.
Byfield, et al., Endothelial Actin and Cell Stiffness is Modulated by Substrate Stiffness in 2D and 3D, J. Biomech., 2009, 42(8):1114-1119.
Celli, et al., Quantitative Imaging Reveals Heterogeneous Growth Dynamics and Treatment-Dependent Residual Tumor Distributions in a Three-Dimensional Ovarian Cancer Model, Journal of Biomedical Optics, 2010, 15(5):051603-1-051603-10.
Chan, et al., OCT-Based Arterial Elastography: Robust Estimation Exploiting Tissue Biomechanics, Optics Express, 2004, 12(19):4558-4572.
Cuche, et al., Spatial Filtering for Zero-Order and Twin-Image Elimination in Digital Off-Axis Holography, Applied Optics, 2000, 39(23):4070-4075.
Dembo, et al., Stresses at the Cell-to-Substrate Interface During Locomotion of Fibroblasts, Biophysical Journal, 1999, 76:2307-2316.
Desai, et al., Microfabricated Post-Array-Detectors (mPADs): An Approach to Isolate Mechanical Forces, Journal of Visualized Experiments, 2007, 7, 4 pages.
Dikovsky, et al., Defining the Role of Matrix Compliance and Proteolysis in Three-Dimensional Cell Spreading and Remodeling, Biophysical Journal, 2008, 94:2914-2925.
Discher, et al., Tissue Cells Feel and Respond to the Stiffness of Their Substrate, Science, 2005, 310:1139-1143.
Evans, et al., In Vitro Ovarian Tumor Growth and Treatment Response Dynamics Visualized with Time-Lapse OCT Imaging, Optics Express, 2009, 17(11):8892-8906.
Evans, et al., Substrate Stiffness Affects Early Differentiation Events in Embryonic Stem Cells, European Cells and Materials, 2009, 18:1-14.
Hajjarian, et al., Intravascular Laser Speckle Imaging Catheter for the Mechanical Evaluation of the Arterial Wall, Journal of Biomedical Optics, 2011, 16(2):026005-1-026005-7.
Hajjarian, et al., Evaluating the Viscoelastic Properties of Tissue from Laser Speckle Fluctuations, Scientific Reports, 2012, 2:316, pp. 1-8.
Hariharan, Optical Holography: Principles, Techniques, and Applications, Second Edition, Cambridge Studies in Modern Optics, Cambridge University Press, 1996 [Title Page Only].
Hu, et al., Differential Transmission of Actin Motion Within Focal Adhesions, Science, 2007, 315:111-115.
Huang, et al., Cell Tension, Matrix Mechanics, and Cancer Development, Cancer Cell, 2005, 8(3):175-176.
Ingber, Mechanical Signaling and the Cellular Response to Extracellular Matrix in Angiogenesis and Cardiovascular Physiology, Circulation Research, 2002, 91:877-887.
Ingber, Can Cancer Be Reversed by Engineering the Tumor Microenvironment?, Semin. Cancer Biol., 2008, 18(5):356-364.
Irimia, Microfluidic Technologies for Temporal Perturbations of Chemotaxis, Annu. Rev. Biomed. Eng., 2010, 12:259-284.
Jemal, et al., Cancer Statistics, 2009, CA Cancer J. Clin., 2009, 59:225-249.
Kim, Tomographic Three-Dimensional Imaging of a Biological Specimen Using Wavelength-Scanning Digital Interference Holography, Optics Express, 2000, 7(9):305-310.
Leung, et al., A New Microrheometric Approach Reveals Individual and Cooperative Roles for TGF-B1 and IL-1B in Fibroblast-Mediated Stiffening of Collagen Gels, The FASEB Journal, 2007, 21:000-000, 10 pages.
Lewis, Fast Template Matching, Vision Interface 95, Canadian Image Processing and Pattern Recognition Society, Quebec City, Canada, May 15-19, 1995, pp. 120-123.
Marquet, et al., Digital Holographic Microscopy: A Noninvasive Contrast Imaging Technique Allowing Quantitative Visualization of Living Cells with Subwavelength Axial Accuracy, Optics Letters, 2005, 30(5):468-470.
Mason, et al., Optical Measurements of Frequency-Dependent Linear Viscoelastic Moduli of Complex Fluids, Physical Review Letters, 1995, 74(7):1250-1253.
Montfort, et al., Submicrometer Optical Tomography by Multiple-Wavelength Digital Holographic Microscopy, Applied Optics, 2006, 465(32):8209-8217.
Nadiarnykh, et al., Alterations of the Extracellular Matrix in Ovarian Cancer Studied by Second Harmonic Generation Imaging Microscopy, BMC Cancer, 2010, 10:94, 14 pages.
Nadkarni, et al., Characterization of Atherosclerotic Plaques by Laser Speckle Imaging, Circulation, 2005, 112:885-892.
Nadkarni, et al., Measurement of Fibrous Cap Thickness in Atherosclerotic Plaques by Spatiotemporal Analysis of Laser Speckle Images, Journal of Biomedical Optics, 2006, 11(2):021006-1-021006-7.
Nadkarni, et al., Measurement of Collagen and Smooth Muscle Cell Content in Atherosclerotic Plaques Using Polarization-Sensitive Optical Coherence Tomography, Journal of the American College of Cardiology, 2007, 49(13):474-481.
Nadkarni, et al., Laser Speckle Imaging of Atherosclerotic Plaques Through Optical Fiber Bundles, J. Biomed. Opt., 2008, 13(5):054016.
Nadkarni, et al., Evaluation of Collagen in Atherosclerotic Plaques: The Use of Two Coherent Laser-Based Imaging Methods, Lasers Med. Sci., 2009, 24:439-445.

(56) References Cited

OTHER PUBLICATIONS

Paszek, et al., Tensional Homeostasis and the Malignant Phenotype, Cancer Cell, 2005, 8:241-254.
Pine, et al., Features of Diffusing Wave Spectroscopy, Physical Review Letters, 1988, 60(12):1134, pp. 35-43.
Reinhart-King, et al., The Dynamics and Mechanics of Endothelial Cell Spreading, Biophysical Journal, 2005, 89:676-689.
Reinhart-King, et al., Cell-Cell Mechanical Communication Through Compliant Substrates, Biophysical Journal, 2008, 95:6044-6051.
Schnars, et al., Digital Recording and Numerical Reconstruction of Holograms, Measurement Science and Technology, 2002, 13:R85-R101.
Shreiber, et al., Effects of PDGF-BB on Rat Dermal Fibroblast Behavior in Mechanically Stressed and Unstressed Collagen and Fibrin Gels, Experimental Cell Research, 2001, 266:155-166.
Stevenson, et al., Light Forces the Pace: Optical Manipulation for Biophotonics, Journal of Biomedical Optics, 2010, 15(4):041503-1-041503-21.
Tan, et al., Cells Lying on a Bed of Microneedles: An Approach to Isolate Mechanical Force, PNAS, 2003, 100(4):1484-1489.
Ulrich, et al., The Mechanical Rigidity of the Extracellular Matrix Regulates the Structure, Motility, and Proliferation of Glioma Cells, Cancer Res., 2009, 69(10):4167-4174.
Yelin, et al., Three-Dimensional Imaging Using Spectral Encoding Heterodyne Interferometry, Optics Letters, 2005, 30(14):1794-1796.
Yip, et al., Calcification by Valve Interstitial Cells is Regulated by the Stiffness of the Extracellular Matrix, Arterioscler. Thromb. Vasc. Bia, 2009, 29:936-942.
PCT International Search Report and Written Opinion, PCT/US2012/025783, Jun. 21, 2012.
PCT International Preliminary Report on Patentability, PCT/US2012/025783, Aug. 29, 2013.

* cited by examiner

LASER SPECKLE MICRORHEOMETER FOR MEASURING MECHANICAL PROPERTIES OF BIOLOGICAL TISSUE

CROSS-REFERENCE TO RELATED APPLICATIONS

This application represents the national stage entry of PCT International Application No. PCT/US2012/025783 filed on Feb. 20, 2012, which claims the benefit of U.S. Provisional Patent Application No. 61/444,192 filed on Feb. 18, 2011. The disclosure of each of these applications is hereby incorporated by reference.

TECHNICAL FIELD

The present invention relates to measurements of mechanical properties of a biological tissue and, more particularly, to measurements of such properties with cellular resolution with the use of a laser speckle microrheometer.

BACKGROUND ART

It is recognized that progression of such diseases as cancer and atherosclerosis, for example, and other debilitating disorders including neurodegenerative disease and osteoarthritis, is accompanied by changes in stiffness of biological tissue. Recent advances in the field of mechanobiology establish that these changes in the stiffness of the extra-cellular matrix (ECM) are not merely passive consequences of earlier causal events, but may in turn influence the behavior of tissue cells, thereby possibly further exacerbating the disease. The biological cells are mechanosensitive in that they feel, perceive, and respond to the mechanical properties of their ECM microenvironment. For example, a cell senses stiffness by exerting tension as it anchors and pulls on the ECM via focal adhesion sites that involve transmembrane integrins and a network of intracellular mechanosensory proteins. Mechanical cues received from the ECM are relayed and translated by intracellular signaling pathways that, in turn, influence cell morphology, differentiation, proliferation, contractility and elasticity. Behavior of the cells that have been altered affects a dynamic balance between the ECM production and break down, thereby causing the ECM stiffness to be changed further. As a result, a positive feedback loop is established with consequences that are sometimes detrimental to the cell's health. For example, the altered ECM stiffness can induce epithelial tumor progression, switch on the malignant phenotype in tumor cells, cause smooth muscle cell proliferation in atherosclerosis, enhance the angiogenesis potential of endothelial cells, initiate calcium deposition by interstitial cells in cardiac valves, modulate stem cell differentiation, and induce cell apoptosis. The cellular response was shown to be regulable via tuning the ECM mechanical properties to values comparable with those of a normal tissue.

Changes in the mechanical properties of the ECM may provide the early detectable signs of the disease onset that likely precede aberrant intracellular signals. Moreover, by engineering the ECM mechanical properties it may be possible to reverse the progress of the disease. Therefore, the capability to measure and monitor minute changes in the ECM stiffness at the size scale sensed by cells (referred to herein as cellular spatial scale) is vital in advancing current understanding in mechanobiology and may, quite possibly, enable not only the detection of the initial onset of a number of critical diseases but also the guidance of an early therapeutic intervention in case of such diseases.

The currently used systems and method are adapted to in vitro studies that evaluate the impact of global (or bulk) ECM mechanical properties on condition of the cells. In contradistinction, however, the biological cells probe the stiffness of their local microenvironment on a substantially smaller scale, via micron-sized focal adhesions and, due to tissue heterogeneities and matrix remodeling, the ECM micromechanical environment that a cell perceives is vastly different from the bulk mechanical environment. The majority of the hypotheses in mechanobiology, generated from experiments in monolayer cell models, fail to recapitulate the complex three-dimensional (3D) environment that a cell experiences in vivo. It is well established that cellular behavior is profoundly different in 3D models where the influence of the ECM composition and stiffness is far more complicated compared to the two-dimensional (2D) monolayer models. Accordingly, there remains a question of how mechanobiological relationships translate into biologically relevant 3D disease models and in clinically relevant systems in vivo. However, no means exists today that enable measurements of the ECM stiffness in 3D at microscopic size scales relevant to the microenvironment of a biological cell. The present invention offers such means.

SUMMARY OF THE INVENTION

Embodiments of the present invention provide a method for forming a three-dimensional (3D) map, of a micromechanical property of a biological tissue, that has microscopic spatial resolution in all three dimensions. Such method includes calculating two-dimensional (2D) distributions of a viscoelastic parameter representing the mechanical property at respectively corresponding tissue depths. Each 2D distribution is calculated from optical data representing light scattered only by a biological tissue layer that is located at the respectively corresponding depth and that is limited in thickness by a parameter related to a coherence length of used light. The method further includes mapping the calculated 2D distributions into a 3D data set representing the 2D distributions in relation to the depths of corresponding tissue layers.

In one embodiment, the calculation of 2D distributions includes calculating each 2D distribution based on optical data representing light scattered only by a biological tissue layer defined via interferometric coherence-gating of light detected with said optical detector. In a related embodiment, the calculation of 2D distributions includes a calculation based on optical data that represents Brownian motion displacements of intrinsic light-scattering particles of the biological tissue. In a specific embodiment, for example, the calculation of 2D distributions includes detecting an optical interferogram by overlapping a sample distribution of light (that has been transmitted to the biological tissue through a sample train of optical components and has interacted with the tissue layer) and a reference distribution of light (that has passed through a reference train of optical components including an optical delay line having a variable optical delay length). The sample and reference distributions of light are mutually coherent. The specific embodiment of the method further contains mathematically reconstructing the detected interferogram to form a spatially-filtered optical interferogram. Optionally, the depth at which the tissue layer is located is defined by an optical distance between a component of at least one of the sample and reference trains of optical components and the biological tissue. Optionally, the calculation of the 2D distribution involves repositioning of an optical component of the sample train and adjusting a variable optical delay length by an amount optically matching said incremental amount and, in particular, changing the optical delay length.

An embodiment of the method optionally further includes at least one of color-coding of the calculated 2D distribution of the viscoelastic parameter (carried out depending at least in part on a value of said viscoelastic parameter) and displaying at least one of said color-coded 2D distribution and the 3D data set into which the calculated 2D distributions are mapped.

Embodiments of the present invention additionally provide for a method for forming a three-dimensional (3D) map of a micromechanical property of a biological tissue with microscopic resolution. Such method includes: (i) detecting an optical interferogram, at the optical detector, by overlapping the mutually coherent sample distribution of light (that has been transmitted to the biological tissue through a sample train of optical components and has interacted with a tissue layer) and reference distribution of light (that has passed through a reference train of optical components including an optical delay line having a variable optical delay length); (ii) calculating a two-dimensional (2D) distribution of a viscoelastic parameter representing the mechanical property of the biological tissue from optical data representing speckle fluctuations and corresponding to the detected interferogram; and (iii) associating the calculated 2D distribution of the viscoelastic parameter with a depth of the tissue layer within the biological tissue. The depth of the layer, with which the sample distribution of light has interacted, within the tissue is defined by an optical distance between a component of at least one of the sample and reference trains of optical components and the biological tissue. The method further includes mathematically reconstructing said optical interferogram including spatially-filtering said optical interferogram.

The process of detecting an optical interferogram may include detecting a sample distribution of light that has been scattered only by a tissue layer located at a predetermined depth of the tissue. Alternatively or in addition, the process of calculating a 2D distribution of a viscoelastic parameter may include calculating a 2D distribution of such parameter based at least in part on data representing Brownian motion displacements of intrinsic light-scattering particles of the biological tissue.

In a related embodiment, the method additionally includes changing the optical distance by an incremental amount and repeating the steps of detecting, calculating, and associating as defined above in order to obtain and characterize a 2D distribution of the viscoelastic parameter corresponding to a layer of tissue located at a different, changed depth within the tissue sample. Generally, the incremental amount by which the optical distance is changed does not exceed 20 microns and is preferably smaller than 10 microns and more preferably smaller than 5 microns. In a specific implementation, changing the optical distance includes repositioning of an optical component of the sample train and adjusting a variable optical delay length by an amount optically matching said incremental amount. Detection of an optical interferogram optionally includes detection of a sample distribution of light that is defocused with respect to a boundary of the biological tissue, while changing the optical distance optionally includes adjusting the variable optical delay length. The method may additionally include displaying calculated 2D distributions as a 3D map of a geometrical distance parameter corresponding to the optical distance.

The method may additionally include transforming 2D distributions calculated as a functions of depths of the tissue layers into the 3D map representing a 3D microscopically-resolved distribution of a mechanical property of the tissue.

Alternatively or in addition, the method optically includes at least one of color-coding the calculated 2D distribution of the viscoelastic parameter depending at least in part on a value of the viscoelastic parameter and displaying the calculated 2D distribution of the viscoelastic parameter as a function of a geometrical distance parameter corresponding to said optical distance.

Embodiments of the invention further provide a visually-perceivable representation of a three-dimensional (3D) distribution of stiffness of a biological tissue formed a process including (i) an acquisition of multiple sets of optical data from light distributions at an optical detector (such that each of these light distributions corresponds to an optical interferogram formed by spatially overlapping sample and reference mutually coherent beams of light, where the sample beam of light interacted with the biological tissue and the reference beam of light passed through a line of variable optical delay, different interferograms corresponding to at least one of different optical delays and different depths of the biological tissue (ii) a determination, from the acquired multiple sets of optical data, of respectively corresponding two-dimensional (2D) distributions of a viscoelastic modulus of the biological tissue; and (iii) displaying the determined 2D distributions for visualization as a function of a parameter representing at least one of said different optical delays and different depths of the biological tissue.

In one embodiment, at least one of the acquisition of multiple sets of optical data and the determination of the 2D distributions is made at least in part based on Brownian motion displacements of intrinsic light-scattering particles of the biological tissue.

In the provided visually-perceivable representation, at least one of the 2D portions of the representation is color-coded in relation of values of the viscoelastic modulus. In a specific embodiment, the visually-perceivable representation includes an image representing, with microscopic resolution, a volumetric distribution of a viscoelastic modulus in said biological tissue.

Moreover, embodiments of the invention, provide a computer program product for determining a volumetric distribution of a micromechanical parameter characterizing a biological tissue, the computer program product containing a computer usable tangible medium having computer readable program code thereon, which computer readable program includes at least (i) program code for calculating two-dimensional (2D) distributions of a viscoelastic parameter representing the micromechanical property at tissue depths that respectively correspond to the 2D distributions (where each 2D distribution is calculated from optical data representing light scattered only by a biological tissue layer located at the respectively corresponding depth and that is limited in thickness by a parameter related to a coherence length of said light, said light being detected with an optical detector); and (ii) program code for mapping the calculated 2D distributions into a 3D data set representing, with microscopic resolution, these 2D distributions in relation to the corresponding depths of the tissue sample. In addition, the computer program product optionally includes at least one of program code for calculating a 2D distribution from optical data representing light scattered only by a biological tissue layer defined via interferometric coherence-gating of light detected at the optical detector; program code for color-coding a calculated 2D distribution of the viscoelastic parameter depending at least in part on a value of the viscoelastic parameter; and program code for displaying at least one of a color-coded 2D distribution and the 3D data set into which the 2D distributions have been mapped.

The embodiment of a computer program product may optionally include program code for reconstructing an optical interferogram formed by overlapping a sample distribution of light (which has been transmitted to the biological tissue through a sample train of optical components and has interacted with a tissue layer) and a reference distribution of light (which has passed through a reference train of optical components including an optical delay line having a variable optical delay length). The reconstruction of an optical interferogram is configured, at least in part, to produce a spatially-filtered interferogram. Finally, an embodiment may also include program code for adjusting the variable optical delay length of the reference train of optical components by an incremental amount.

BRIEF DESCRIPTION OF THE DRAWINGS

The invention will be more fully understood by referring to the following Detailed Description in conjunction with the Drawings, of which:

FIG. 3A: a bright-field microscopy image. FIG. 3B: a laser-speckle pattern. FIG. 3C: a reconstructed color-map of stiffness.

DETAILED DESCRIPTION

In accordance with preferred embodiments of the present invention, a Laser Speckle Microrheometer (LSM) system is disclosed, as well as a corresponding method of depth-resolved speckle microrheometry, that facilitate the measurements of 3D mechanical properties of a biological tissue with cellular-scale (on the order of several microns, for example 1 to 20 microns, preferably 1 to 10 microns, and more preferably 1 to 5 microns) resolution with high sensitivity in order to monitor small changes in the ECM stiffness.

References throughout this specification to "one embodiment", "an embodiment", "a related embodiment", or similar language mean that a particular feature, structure, or characteristic described in connection with the referred to "embodiment" is included in at least one embodiment of the present invention. Thus, appearances of the phrases "in one embodiment", "in an embodiment", and similar language throughout this specification may, but do not necessarily, all refer to the same embodiment. It is to be understood that no portion of disclosure, taken on its own and in possible connection with a figure, is intended to provide a complete description of all features of the invention.

In addition, the following disclosure may describe features of the invention with reference to corresponding drawings, in which like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in claims appended to this disclosure is intended to be assessed in light of the disclosure as a whole.

Stiffening of tissue has been an informative indicator of various medical conditions. Desmoplastic stiffening that accompanies neoplasia, for example, has traditionally provided a viable metric to detect tumors in the clinic via physical palpation or by imaging tools. Recent studies indicate that this increased stiffening is not merely a result of tumorigenesis, but may actively drive oncogenic signaling and regulate tumor growth, invasion and metastasis. For example, the ECM stiffness has been shown to regulate tumor cell morphology, proliferation, migration, differentiation, and malignant transformation. Stiffness gradients can drive migration of cancer-associated fibroblasts and macrophages and impact myofibroblast contractility. Stromal stiffness also influences treatment efficacy: the stiffer ECM is more resistant to drug penetration, while heightening cell resilience to drug induced apoptosis, which suggests mechanical information is crucial in order to develop therapies that counter drug resistance. Although the mechanisms by which the ECM mechanics orchestrate tumor evolution remain unclear, there are indications that cells sense stiffness via transmembrane integrin receptors that couple the ECM with the actin cytoskeleton. The ECM stiffening has been shown to induce integrin clustering, reinforces cell-ECM focal adhesions and activates mechanosensory proteins that trigger mitogenic signaling and impact actomyosin contractility, causing further ECM stiffening. As a result, a positive feedback loop is established connecting extracellular mechanical cues with intracellular signaling pathways that regulate cell proliferation, differentiation and migration. Tumor pathogenesis is thus driven by this cooperative dialogue between ECM mechanics and oncogenic signaling, underscoring the fact that knowledge of the ECM mechanical properties is equally crucial in advancing our understanding of cancer etiology, and developing new therapies and prognostic indicators to manage cancer Current insights on this mechano-biological dialogue between the ECM and cell signaling however are mostly limited to 2D monolayer cultures that fail to recapitulate the complex 3D microenvironment a cell perceives in vivo. Yet, it is well established that cell behavior is profoundly different in 3D ECMs likely due to distinct 3D fiber architecture and compliance. Furthermore, majority of the hypotheses in the field have been generated by studying the impact of bulk stiffness integrated over the entire substrate. Cells however probe the ECM via micron-sized focal adhesions; and due to micro-scale variations in fiber density, microstructure and pore size the mechanical environment a cell perceives is vastly different from the bulk environment. Due to these limitations, crucial questions remain on how ECM mechanical regulation translates in biologically relevant disease systems.

Conventionally, mechanical properties of a tissue sample are determined via the frequency-dependent viscoelastic modulus, $G^*(\omega)$, in accord with principle of mechanical rheometry, when by the sample is sheared, for example, within a parallel plate to evaluate the stress caused in the sample over a limited range of oscillation frequency $\omega$. Substantial manipulation of the tissue sample is required in order to effectuate such measurements, thereby rendering the mechanical rheometer practically unsuitable for evaluating mechanical properties of live cells. Therefore, only a static snapshot of bulk mechanical properties averaged over large sample volumes can be obtained prior to cell seeding (such as, for example, culturing cells on a matrix prior to cell growth and proliferation]. Accordingly, serial monitoring of the ECM stiffness with the use of a conventional mechanical rheometer is not feasible.

Related art also discussed nano-indentation tools that probe stiffness of the tissue surface and map this surface on a micro-scale (about 1 to 10 µm). This methodology, however, fails to provide depth-resolved measurements of the stiffness parameter(s). Another approach, referred to as bead-twisting microrheology, has been recently reported to determine a degree of rotation of micro-beads (seeded in a tissue) in a twisting magnetic or optical field and to evaluate local matrix properties based on the extent of bead rotation. While this technique demonstrates a capability for 3D measurements, difficulty in achieving uniform bead distribution limits practical application to the bead microenvironment.

We previously demonstrated the use of a so-called Laser Speckle Rheology (LSR) approach (that utilizes Laser Speckle Imaging or LSI), which utilizes laser-speckle imaging, to non-destructive analysis of tissue. The laser-speckle based characterization of the tissue utilizes dynamic light scattering (DLS) principles, according to which the mean square displacements (MSD) of light-scattering particles relate to the viscoelastic susceptibility of the material. According to the LSR methodology, the sample is illuminated with coherent light and images of time-varying laser speckle patterns (or, more generally, optical data corresponding to intensity fluctuations representing light scattered by the elements of the ample) are acquired using a high speed detector (for example, a CMOS camera). Laser speckle, as a phenomenon reflecting the interference of coherent light scattered by the sample, is dynamically modulated by the Brownian motion of light-scattering elements and particles which, in turn, is influenced by the viscoelastic susceptibility of the medium surrounding the light-scattering elements. Generally, the laser speckle concept is known and for that reason is not discussed here in any significant detail. The rate of speckle modulations was shown to closely relate to the mechanical properties of tissue and, in particular, to a viscoelastic modulus $G^*(\omega)$, sometimes referred to as the complex shear modulus and defined in terms of a ratio of tissue sample stress to strain applied to the sample. The real part of $G^*(\omega)$, $G'(\omega)$, referred to as the elastic or storage modulus, represents a measure of solid-like behavior of the tissue sample. The imaginary part $G''(\omega)$, which is out of phase with the applied strain, is the viscous or loss modulus and represents a measure of viscous energy dissipation by the tissue sample. A diagram illustration a typical device currently used for characterization of laser speckle is presented in FIG. 1A, where LS denotes light source (such as a laser, for example), M is a mirror, P is a polarizer, BS indicates a beamsplitter, BE is a beam expander, L1,L2 are the lenses, S is a sample, and DET and PC are a detector and a computer system respectively. Such device and similar currently-used devices have a noticeable shortcoming in that they average the acquired optical data over the volume of the tissue sample (thus enabling evaluation of bulk characteristics, on the scale of about 1 $mm^3$) As a result of such spatial averaging, the depth-resolved information about the tissue is not acquired and, instead, is lost.

In order to enable measurement of the ECM micromechanical properties resolved in three dimensions and to obtain volumetric data, the LSM modality described in this application is adapted to combine the acquisition of full-field speckle frames with the application of dynamic light-scattering principles and interference microscopy to detect depth-resolved laser speckle modulations with the resolution of at least 1 to 20 µm or better (for example, of about 10 microns or better, and more preferably of about 5 microns or better). According to the idea of the invention, optical data representing depth-resolved images of interference (between light scattered and/or diffused by the tissue sample and a reference beam of light) is acquired and analyzed with the use of image-reconstruction methods to extract depth-resolved speckle images. The following analysis of such depth-resolved speckle images, involving dynamic light scattering principles, produces the determination of viscoelastic modulus corresponding to different depths of the tissue, from the speckle fluctuations. Consequently, the determination of micromechanical and microstructural properties of the tissue sample is performed with a single integrated instrument, thereby enabling the investigation of mechanosensitive interactions of living cells with their ECM in 3D in real time.

In contradistinction with the conventional mechanical rheometer, the use of the proposed LSM modality requires no sample manipulation, thereby rendering this device and method uniquely suited for evaluating the ECM of live cells. The LSM affords a large dynamic range (~10 Pa-1 kPa) of the viscoelastic modulus measurements to facilitate evaluation of tissues and biomimetic tissue matrices relevant to a variety of biological tissues, and possesses high sensitivity to small changes in in micromechanical properties of the tissue (corresponding to a detection of the viscoelastic modulus having a value of at least 1 Pa or lower, preferably 0.1 Pa or lower, and most preferably about 0.01 mPa). Furthermore, embodiments of the LSM are adapted to measure $G(\omega)$ over an oscillating frequency range from about 0.001 kHz to about 1 kHz (that is up to 3 orders of magnitude larger than that provided by a mechanical rheometer).

Figure 1A:
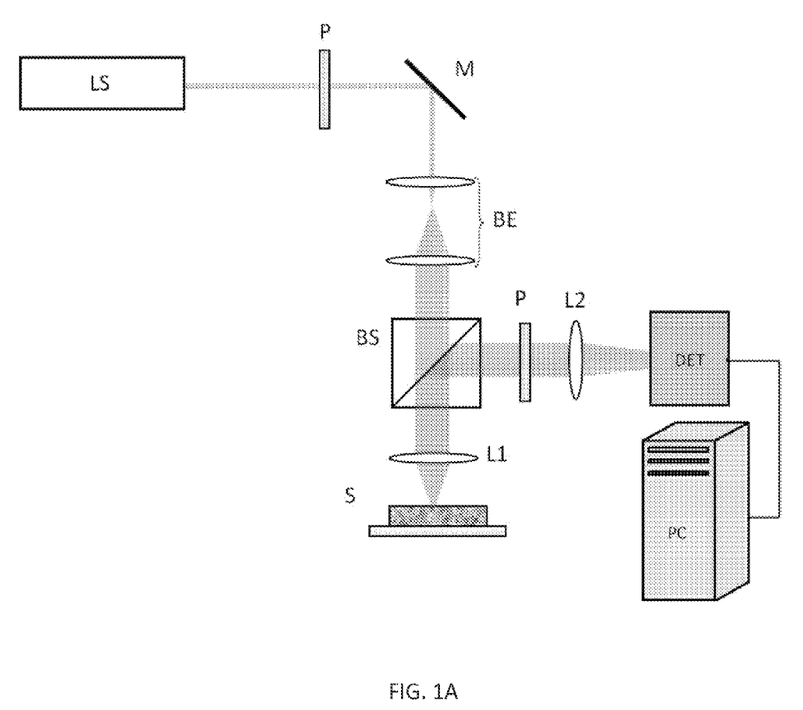
FIG. 1A is a diagram of a conventional set-up for laser speckle measurements.
Figure 1B:
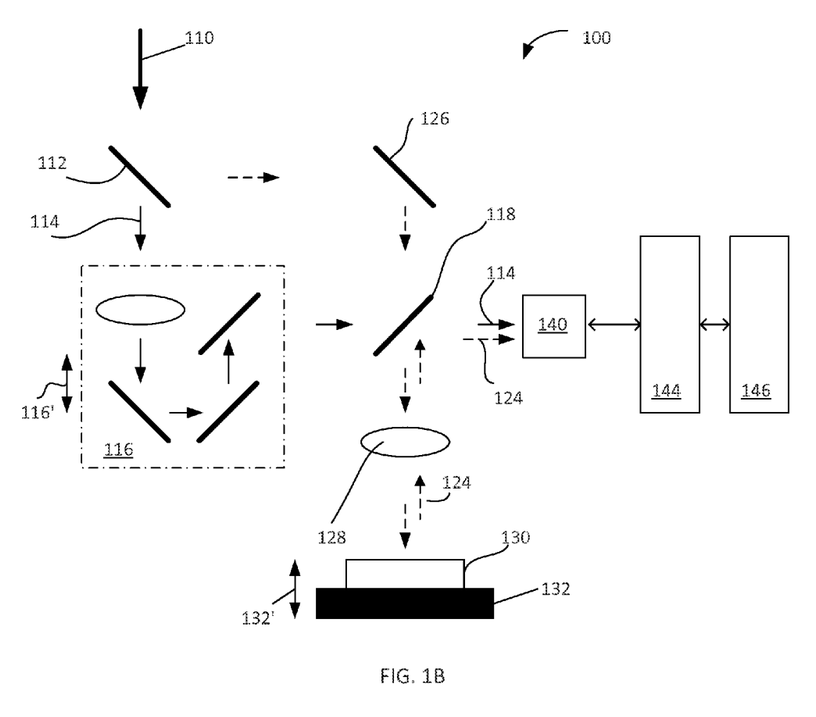
FIG. 1B is a diagram showing schematically an embodiment of the system of the invention.

According to an embodiment 100 of the laser-speckle microrheometer of the invention, schematically shown in FIG. 1B, a beam 110 of light from a source of coherent light (such as a laser, in one example, no shown) is split with an appropriate beam-splitter 112 between sample and reference arms of an interferometer such as, for example, a Mach-Zehnder interferometer. (It is appreciated that a different type of interferometric system can be appropriately used instead.) A portion 114 of light passing through the reference arm of the interferometer. The reference arm of the interferometer contains an optical delay line 116, adjustable as shown with an arrow 116', and, optionally, additional optical components such as refractors, reflectors, optical filters, and the like. Having traversed the reference arm, the portion 114 of light is spatially overlapped (as shown, with the use of a beam-splitter 118) with a portion of light 124 that has traversed the sample arm of the interferometer (defined by the beam-splitters 112, 126, 118, a lens 128 such as a microscope 10× objective, NA=0.25 for example and, optionally, additional not shown optical components) and interacted with a tissue sample 130 placed on a repositionable sample holder 132. The resulting time-dependent, interferometric image of a tissue layer, positioned at a tissue-sample depth that is defined by an optical length of the sample arm that is equal to that of the reference arm, is registered with an optical detector 140 such as a CMOS camera (for example, at a 1 kHz frame rate within a time-window of 2 seconds). The thickness of this particular tissue layer is also specifically defined via coherence-gating (interferometric gating) of light at the detector 140 in that a registered interferogram is formed with the use of light 124 scattered only at the depths of the sample 130 that are defined by coherence length of light 110. (Indeed, interference between light distributions of the sample and reference arms occurs at the detector plane when the optical path lengths of the reference and sample arms are matched to within the coherence length.) As a result, the interferogram associated with each depth of the sample 130 is substantially free of contributions of light scattered from other depths in the biological tissue outside of the tissue layer defined by the interferometric set up. In one embodiment, a low coherence length laser source is used.

Time-resolved images are measured over a finite time period, for example over 1-10 seconds to measure laser speckle fluctuations caused by Brownian motion displacements of light scattering particles at each depth. By scanning the collimated illumination beam across the sample or translating the stage large regions of interest of the tissue can be evaluated.

Optically-acquired interferometric data representing such interferometric image is further processed with a data-acquisition and processing system 144. (A separate measurement of the laser speckle optical irradiance defined by the sample tissue 130 can be optionally performed with the use of the embodiment 100 when light 114 in the reference arm is blocked, i.e. when the reference arm of the interferometer is disengaged). Imaging data representing a 2D interferometric pattern and a 2D laser speckle (LS) pattern, produced by the (interferometrically defined) tissue layer of the sample 130 within the field of view of the lens 128, are further processed by the pre-programmed data processing system 144 to determine a 2D map of distribution of mechanical parameter(s) of the tissue sample with cellular resolution afforded by the LS imaging.

To add an axial dimension to the LS microrheometric measurement, the depth-dependent (with interferometrically-defined resolution of a few microns, for example of about 1 to about 20 microns) time-varying data is acquired, generally, by scanning an optical component of either the sample or reference arm of the device 100. In one example, the axial scanning through the tissue sample 130 can be enabled by sequentially changing a distance between the objective 128 and the tissue sample 130 (such as by repositioning the sample holder 132 with respect to the lens 128 as shown with an arrow 132') and thereby refocusing light traversing the sample arm of the interferometer at different depths within the sample 130. In another example, the sample 130 is illuminated through the lens 128 with a substantially defocused light and the determination of a depth at which a given tissue layer is chosen for interferometric imaging is carried out by readjustment of the variable optical delay line 116, whereby its length is changed by a predetermined incremental amount which, in a specific case, may be defined by the coherence length of light 110. (Alternately, interferograms can be obtained by scanning over multiple wavelengths and depth-resolved images are reconstructed from interferograms that are recorded at multiple wavelengths.) In any instance, each of the acquired sets of data represents a coherence-gated 2D interferogram and is associated with a corresponding depth of the biological tissue sample 130.

Further, the acquired tissue-depth dependent sets of 2D interferometric data are mapped into a 3D data set in relation with the corresponding tissue depth at which such 2D data sets were measure. From the 3D data set, the pre-programmed data processing system 144 determines a 3D distribution of stiffness of the ECM sensed by cells of the tissue sample 130.

The interferograms acquired with an embodiment of the LSM system such as the embodiment of FIG. 1A are further processed to reconstruct 2D images corresponding to multiple depths of the sample 130 with the use of mathematical formalisms well established for holographic image reconstruction. See, for example, Schnars et al., in *Measurement Sci. Tech.*, 2002; 13:R-85-R101); Cuche et al., in Appl. Opt. 2000; 39; 4070-4075); Hariharan (Optical holography: Principles, techniques, and application, Cambridge Univ. Press, 1996); and Marquet P. et al., in *Opt Letts*. 2005; 30:468-470; and Montfort F. et al., in *Applied Opt.* 2006; 45:8209-8217.

Descriptions of mathematical formalisms for holographic image reconstruction taught in the abovementioned publications are incorporated herein by reference. A reconstruction algorithm of the present invention includes, in relevant part, filtering an interferogram (associated with light 124 scattered by a tissue layer at particular depth of the tissue sample 130) in Fourier domain to at least eliminate the unwanted zero-order diffraction and conjugate images, thereby forming a filtered interferogram. Because an interferogram can be considered a diffraction grating (as far as a wavefront incident onto the interferogram in concerned), a product of the filtered interferogram and the complex amplitude of the light-beam in the reference arm of the interferometer (such as the embodiment 100) is formed from which the 2D image is extracted, under the Fresnel diffraction approximation. A sequence of time-varying 2D images corresponding to tissue layers located at different tissue sample depths are stitched together to form a time-varying 3D-image array containing optical data that represent both microstructural and speckle information about the tissue sample 130.

In one instance, for example, the time-varying viscoelastic modulus characteristic is derived for each value of optical delay (established by the appropriate alignment of the reference arm of the interferometer of FIG. 1B) based on the acquired optical data representing irradiance fluctuations across the registered laser speckle field, from a speckle intensity decorrelation function $g_2(t)$ that characterizes the rate of speckle intensity fluctuations and is empirically expressed, in terms of the MSD $\langle \Delta r^2(t) \rangle$ of light-scattering particles, as $$g_2(t) = \beta^2 \exp\left(-2\gamma\sqrt{k^2\langle\Delta r^2(t)\rangle + \frac{3\mu_a}{\mu_s(1-g)}}\right) + 1 = \qquad (1)$$

$$= \beta^2 \exp\left(-2\gamma\sqrt{k^2 r_0^2(1-e^{-t/\tau_D}) + \frac{3\mu_a}{\mu_s(1-g)}}\right) + 1$$

where k is the wave number in the blood sample, $\gamma$ is an experimental parameter related to the size(s) of scattering particle(s) of the tissue sample and polarization state of light, $\beta$ is a parameter corresponding to the degree of coherence of light detected after being scattered by the tissue sample, and $$\frac{3\mu_a}{\mu_s(1-g)}$$

defines the optical properties of the sample (via $\mu_a$, which relates to an absorption coefficient of the tissue sample, and $\mu_s$, which relates to the scattering coefficient of the tissue sample).

In order to experimentally determine the $g_2(t)$ value corresponding to optical irradiance detected at a particular pixel of the detector 140, the normalized cross-correlation (NCC) of a chosen 3D array of data is computed in the Fourier domain. The maximum NCC value corresponding to that particular pixel is then determined, and $g_2(t)$ is defined by averaging several cross-correlation functions that evolve in time, Optionally, to account for the contribution of static time-independent component of irradiance of light scattered by the sample, the averaged $g_2(t)$ value is normalized by the time-averaged irradiance.

An embodiment of the algorithm further includes determination of the viscoelastic modulus from the MSD data, for each pixel. For the specific model of Eq. (1), for example, $G^*(\omega)$ is determined with the use of a modified algebraic form of the generalized Stokes-Einstein equation that directly relates the MSD of particles in motion to the frequency-dependent bulk viscoelastic modulus $G^*(\omega)$, of the material, via $$|G^*(\omega)| = \frac{kT}{\pi a \langle \Delta r^2(1/\omega) \rangle \Gamma(1+\alpha(\omega))}\bigg|_{t=1/\omega} \qquad (2)$$

where $a$ is the characteristic size of a scattering particle, $\Gamma$ is the gamma function, and $\langle \Delta r^2(1/\omega) \rangle$ is the magnitude of the MSD at $t=1/\omega$. The value of $\alpha(\omega)$ is given by $$\alpha(\omega) = \frac{d\ln\langle\Delta r^2(t)\rangle}{d\ln(t)}\bigg|_{t=1/\omega} \qquad (3)$$

In order to determine a 3D distribution of micromechanical properties of the tissue sample, at each pixel the speckle intensity decorrelation, $g2(t)$, is calculated from the coherence-gated normalized cross-correlation in three-dimensions between the 3D image matrix measured using the interferometric system at time $t=t_0$, with each subsequent time-varying 3D image matrix measured at times $t_i > t_0$. At each pixel, the magnitude of $G^*(\omega)$ is measured using empirical methods described above. The resulting 3D array of discrete $|G^*(\omega)|$ values for each frequency $\omega$ is further processed using spatial filtering and image interpolation techniques to form 3D parameter maps representing a volumetric distribution of tissue sample viscoelasticity.

Optionally, this 3D distribution of the stiffness characteristic of cellular microenvironment is further mapped or transformed into visually perceivable images (such as color-maps, for example) that demonstrate to the user viscoelastic behavior of the tissue sample on cellular level. Accordingly, 3D maps of micromechanical and microstructural characteristics of the tissue sample and corresponding 3D maps of frequency-modulated $G^*(\omega)$ are optionally displayed at a display 146. Contrast of the created color-maps is indicative of micromechanical differences between portions of the mapped tissue.

Figure 2A:
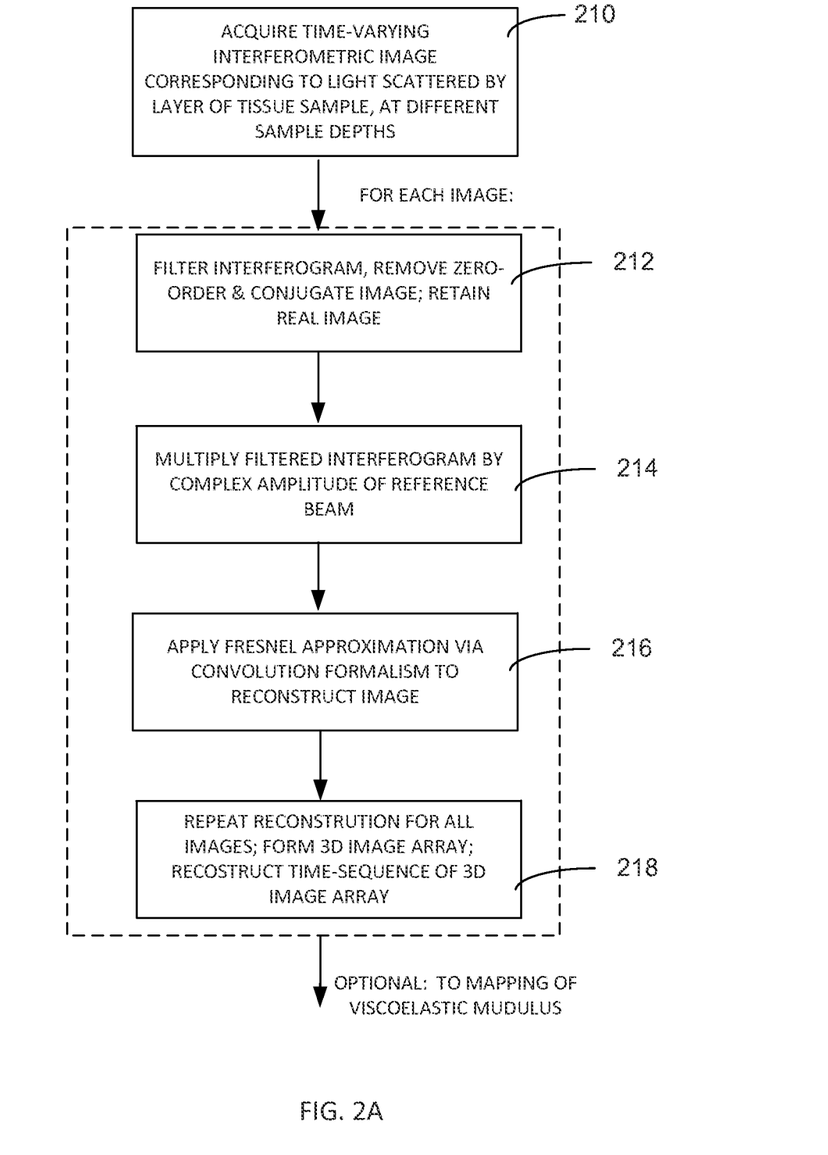
FIG. 2A is a flow-chart illustrating an embodiment of the algorithm for reconstruction of an interferogram for use with an embodiment of the invention.
Figure 2B:
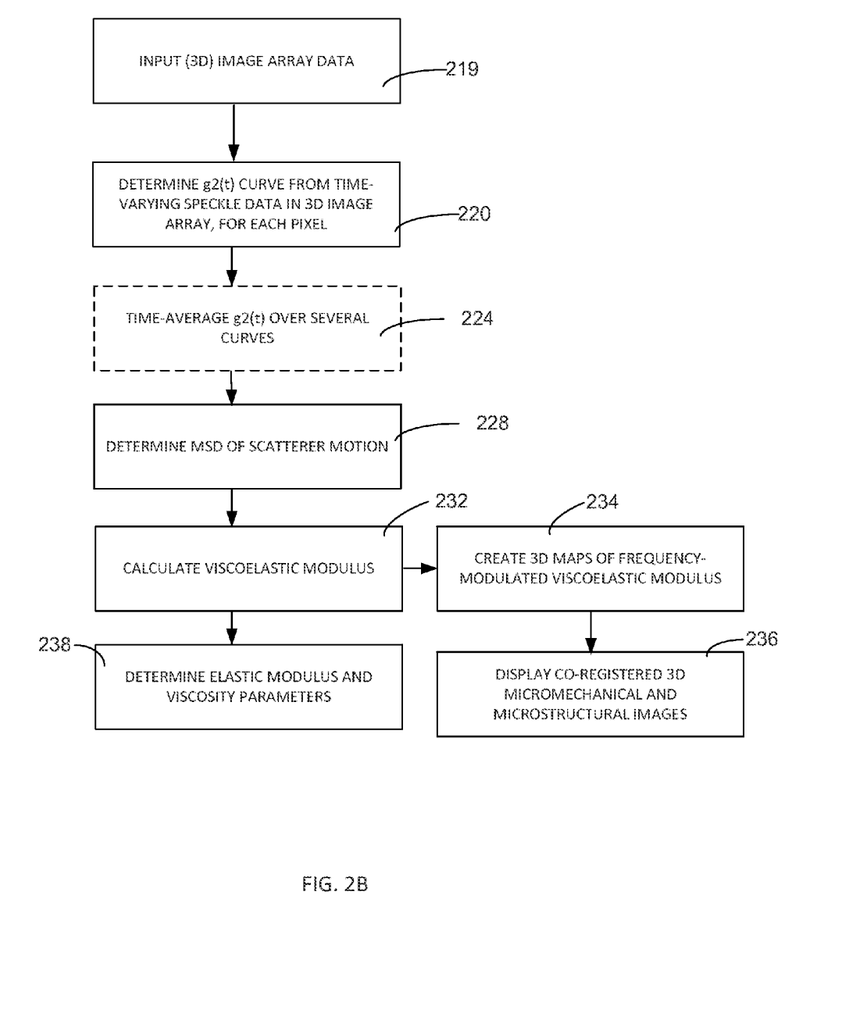
FIG. 2B is a flow-chart illustrating an embodiment of the algorithm for mapping of three-dimensional (3D) distribution of a viscoelastic modulus, of a tissue sample, acquired with the use of an embodiment of the invention.

FIGS. 2A and 2B offer flow-charts that respectively represent embodiments of a method of the invention related to a hologram reconstruction and 3D viscoelastic modulus mapping. Here, major steps if data-processing algorithms of the invention are depicted. In reference to FIG. 2A, for example, at step 210 optical data representing a time-varying interferometric image corresponding to light scattered by a tissue layer that is defined by the instantaneous optical parameters of the employed interferometer and the coherence length of light used for imaging. The acquired optical data is further processed, for example with a computer processor, to spatially filter the interferogram, at step 212, to determine a product the spatially-filtered interferogram with a complex amplitude of the reference beam, at step 214, and to reconstruct the interferometric image at step 216. Such data processing is repeated for each of the interferometric 2D data sets that are further grouped into a 3D data set associating the 2D data sets with respectively corresponding depths of the biological tissue at which tissue layers are located, 218. After, the algorithm may proceed further to mapping of the viscoelastic modulus parameter. In accordance with the flow-chart of FIG. 2B, the 3D interferometric data array is received by the processor at step 219. From the received 3D data array, the decorrelation curves are determined for each pixel of the detector at step 220 and corresponding time-averages values of decorrelation distributions are calculated at step 224. At step 228, the MSD of motion of scatterers of the tissue sample are determined, followed by the calculation of the viscoelastic modulus at step 232. The obtained values of the viscoelastic modulus are optionally mapped into 3D arrays, at step 234, and further displayed, at step 236, as visually-perceivable volumetric representations to the user, optionally together with 3D images of micromechanical characteristics of the tissue sample. Alternatively or in addition, the volumetric elastic modulus and viscosity parameters are determined from the viscoelastic modulus at step 238.

Target operation characteristics of an embodiment of the invention such as the embodiment 100 of FIG. 1 are summarized in Table 1.

Figure 3:
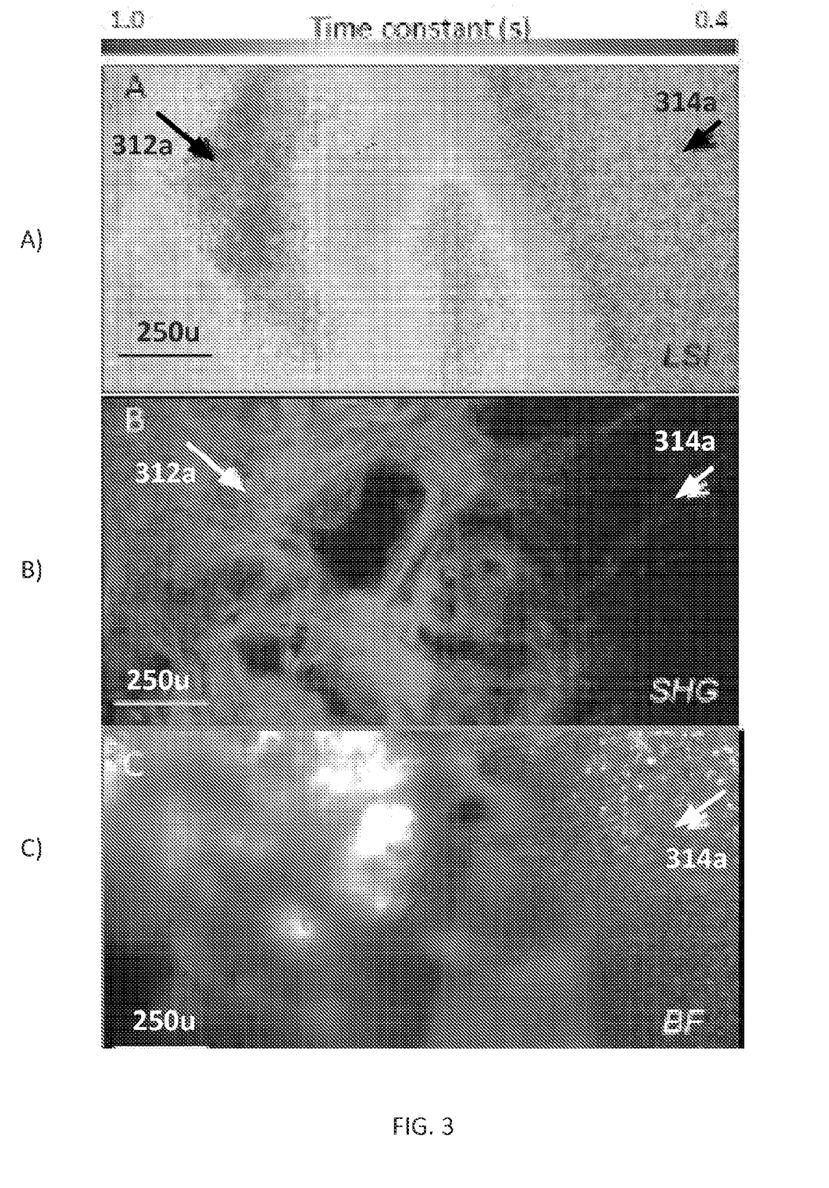
FIGS. 3A, 3B, and 3C are images of a specific tissue sample acquired with the use of three different imaging modalities, and correspondence between identified related portions of these images.

FIGS. 3A, 3B, and 3C provide co-registered images of a human breast tissue with cancer (carcinoma in situ) acquired with bright-field microscopy (FIG. 3C), with the use of second-harmonic frequency imaging, (FIG. 3B), and a color-map of viscoelasticity of the breast tumor tissue obtained with LS-imaging (FIG. 3A). Regions of stiffness, observable in FIG. 3A in red and indicated with an arrow 310a, correlate with the presence of collagen networks in the image of FIG. 3B and indicated with an arrow 314a. Blue regions (indicating low viscosity tissue) of FIG. 3A marked with and arrow 310b are corroborated by imaging of fat-droplets present in the area 314b of FIG. 3C.

Figure 4:
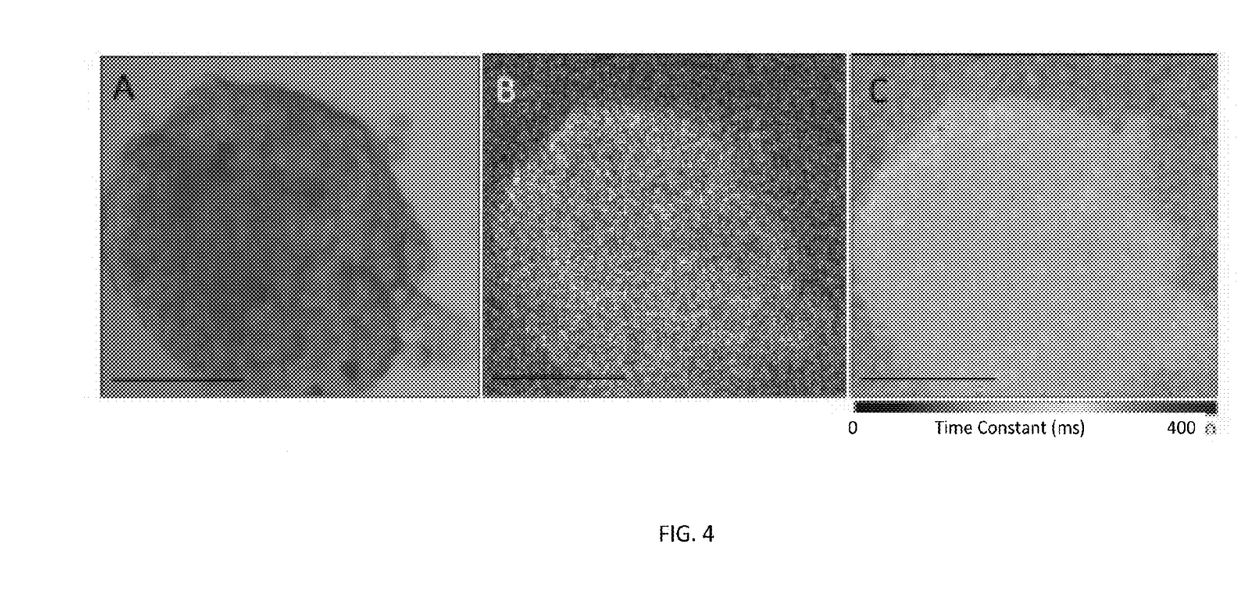
FIGS. 4A, 4B, and 4C are images of a 3D ovarian cancer nodule.

FIGS. 4A, 4B, and 4C illustrate feasibility of laser-speckle based analysis for micromechanical evaluation of 3D ovarian cancer model. FIG. 4A presents a bright-field microscopy image of a multicellular 3D ovarian cancer nodule, while FIG. 4B provides a corresponding a snap-shot image of a corresponding laser speckle pattern. FIG. 4C is a reconstructed color-map showing that the cancer nodule is significantly stiffer than the surrounding ECM, thereby demonstrating that the proposed system and method for evaluation of biological tissue possess sufficient measurement sensitivity.

TABLE 1

| Operational Characteristic | (Range of) Value(s) |
|---|---|
| Spatial Resolution | ~1 um (axial), ~2 um (lateral, transverse) |
| Measurement Depth | ~300 um |
| Field of View (FOV) | ~300 um |
| Working distance | 10 mm |
| Data Storage Rate | ~500 MB/sec |
| Range of Measured G* | about 0.001 Pa to about 1 kPa |
| Accuracy | Correlation: R > 0.7, p < 0.05; deviation of HLSM data from that of mechanical microrheometer not to exceed 10% |
| Range of Frequency ω | about 0.01 KHz to about 1 kHz |
| Frame Rate | ~1 kHz |
| Imaging time per frame | Sample dependent (for example, ~1 to 2 s for softer samples of < 10 kPa; ~10 s for firmer sample of ~10 kPa) |
| Sensitivity (an measurable increment of G*) | about 0.001 Pa |
| Reproducibility | about 90% or higher |

It is appreciated that, in further reference to FIG. 1B, the data acquisition and processing system 144 optionally includes a processor controlled by instructions stored in a memory and programmed to at least store the optical data, analyze the interferograms, carry out the calculation of viscoelastic characteristics of the tissue sample and the determination of the stiffness parameters and their time-evolution based on such viscoelastic characteristics, as well as effectuate creating of color-coded maps of stiffness microstructure as discussed above. In addition, while the invention may be embodied in software, the functions and algorithms necessary to implement the invention may optionally or alternatively be embodied in part or in whole using firmware and/or hardware components known in the art.

While the invention is described through the above-described examples of embodiments, it will be understood by those of ordinary skill in the art that modifications to, and variations of, the illustrated embodiments may be made without departing from the inventive concepts disclosed herein. For example, and in further reference to FIG. 1, while the use of an interferometer in acquitting the optical data provides sufficient rejection of multiply scattered light, additional filtering can be optionally provided by optional use of the polarization-sensitive light detection. To this end, appropriate polarization optics, for instance a polarization beam splitter, can be additionally incorporated into an embodiment As another modification, for accurate determination of $G(\omega)$, time-averaging of $g_2(t)$ distributions may be required. In addition to time averaging, spatial averaging of $g_2(t)$ over neighboring pixels can be conducted or, alternatively, to maintain high spatial resolution for $G(\omega)$ mapping, time averaging can be conducted over longer durations. In order to mitigate artifacts of motion within the measurements system such as the system of FIG. 1, sample 130 can be will be secured on a vibration-isolated platform and, alternatively or in addition, time-averaging and Fourier domain filtering of $g_2(t)$ distributions can be implemented to remove residual instabilities. In another related embodiment, the frequency dependent modulus is determined through the decorrelation-time constant, $\tau$, that is determined from g2(t) curves at each pixel or, alternatively or in addition, over neighboring pixels from the time-varying 3D speckle image series. For example, the time constant $\tau$ can be measured by fitting a single of multiple exponential functions to measure the rate of laser speckle fluctuations.

Various disclosed aspects and features of the invention may be combined in ways not listed above. Accordingly, the invention should not be viewed as being limited to the disclosed embodiment(s).

What is claimed is:

1. A method for forming a three-dimensional (3D) map of a mechanical property of a biological tissue, the method comprising:
   receiving, from an optical detector, optical data representing light scattered only by a biological tissue layer;
   calculating two-dimensional (2D) distributions of a viscoelastic parameter representing the mechanical property of the biological tissue at a plurality of depths including the depth location of the tissue layer and depths outside the depth location of the tissue layer; and
   mapping the 2D distributions into a 3D data set representing the distributions of the viscoelastic parameter in relation to the plurality of depths that indicates a 3D distribution of stiffness of the tissue extra-cellular matrix (ECM) at the depth location of the tissue layer and depths outside the depth location of the tissue layer.

2. A method according to claim 1, further comprising performing interferometric coherence-gating of light detected with the optical detector.

3. A method according to claim 1, further comprising at least one of (i) color-coding a calculated 2D distribution of the viscoelastic parameter depending at least in part on a value of said viscoelastic parameter, and (ii) displaying a visual representation of at least one of said color-coded 2D distribution and said 3D data set showing the stiffness of the extra-cellular matrix (ECM).

4. A method according to claim 1, wherein said calculating includes calculating 2D distributions of a frequency-dependent viscoelastic parameter.

5. A method according to claim 1, further comprising forming an optical interferogram by overlapping a sample distribution of light that has been transmitted to the biological tissue through a sample train of optical components and has interacted with a tissue layer, and a reference distribution of light, which has passed through a reference train of optical components including an optical delay line with a variable optical delay length, wherein the sample and reference distributions of light are coherent.

6. A method according to claim 5, further comprising reconstructing said interferogram in a computer process to form a spatially-filtered optical interferogram.

7. A method according to claim 5, wherein said depth of the biological tissue layer is defined by an optical distance between the biological tissue and an element of at least one of the sample and reference trains of optical components.

8. A method according to claim 7, further comprising changing the optical distance by an incremental amount not exceeding the coherence length.

9. A method according to claim 8, wherein said changing includes repositioning of an optical component of the sample train and adjusting a variable optical delay length by an amount optically matching said incremental amount.

10. A method according to claim 1, wherein said calculating includes calculating 2D distributions from optical data that represents Brownian motion displacements of intrinsic light-scattering particles of the biological tissue.

11. A method according to claim 1, wherein the mapping is correlated in time.

12. A method according to claim 1, wherein the viscoelastic parameter indicates an elastic or viscous modulus of the tissue layer.

13. A method for forming a three-dimensional (3D) map of a mechanical property of a biological tissue, the method comprising:
    detecting an optical interferogram, at the optical detector, by overlapping (i) a sample distribution of light, which has been transmitted to the biological tissue through a sample train of optical components and has interacted with a tissue layer, and (ii) a reference distribution of light, which has passed through a reference train of optical components including an optical delay line having a variable optical delay length, the sample and reference distributions of light being coherent, said position of the tissue layer being defined by an optical distance between the biological tissue and an element of at least one of the sample and reference trains of optical components;
    calculating a two-dimensional (2D) distribution of a viscoelastic parameter representing the mechanical property of the biological tissue from optical data corresponding to the detected interferogram; and
    associating the calculated 2D distribution of the viscoelastic parameter with a depth of the tissue layer within the biological tissue to define one-to-one correspondence between said calculated 2D distribution with said depth of the tissue layer and tissue within the biological tissue surrounding the tissue layer;
    wherein said calculated 2D distribution of the viscoelastic parameter includes information about an extra-cellular matrix relative to the tissue layer.

14. A method according to claim 13, wherein said detecting includes the use of a sample distribution of light that has been transmitted to the biological tissue through a sample train of optical components and has been scattered only by a tissue layer located at a predetermined depth of the biological tissue.

15. A method according to claim 13, wherein said calculating includes calculating a 2D distribution of a viscoelastic parameter based at least in part on data representing Brownian motion displacements of intrinsic light-scattering particles of the biological tissue.

16. A method according to claim 13, further comprising: changing the optical distance by an incremental amount; and repeating said detecting, calculating, and associating.

17. A method according to claim 16, wherein said incremental amount does not exceed 20 microns.

18. A method according to claim 16, wherein said incremental amount does not exceed 5 microns.

19. A method according to claim 16, wherein said changing the optical distance includes repositioning of an optical component of the sample train and adjusting a variable optical delay length by an amount optically matching said incremental amount.

20. A method according to claim 16, further comprising transforming 2D distributions calculated as a function of depths into said 3D map representing a 3D microscopically-resolved distribution, of a mechanical property of the tissue.

21. A method according to claim 13, further comprising at least one of color-coding said calculated 2D distribution of the viscoelastic parameter depending at least in part on a value of said viscoelastic parameter and displaying the calculated 2D distribution of the viscoelastic parameter as a function of a geometrical distance parameter corresponding to said optical distance.

22. A method according to claim 13, wherein said detecting an optical interferogram includes detecting a sample distribution of light that is defocused with respect to a boundary of the biological tissue and changing the optical distance by adjusting a variable optical delay length.

23. A non-transitory, computer-readable storage medium having stored thereon, a computer program that, when executed by a computer, causes the computer to:
    receive, from an optical detector, optical data representing light scattered only by a biological tissue layer;
    calculate two-dimensional (2D) distributions of a viscoelastic parameter representing the mechanical property of the biological tissue at a plurality of depths including the depth location of the tissue layer; and
    map the 2D distributions into a 3D data set representing the distributions of the viscoelastic parameter in relation to the plurality of depths that indicates a 3D distribution of stiffness of extra-cellular matrix (ECM) sensed by cells of the tissue layer.

24. A method for forming a three-dimensional (3D) map of a mechanical property of a biological tissue, the method comprising:
    receiving, from an optical detector, optical data representing light scattered only by a biological tissue layer;
    calculating two-dimensional (2D) distributions of a viscoelastic parameter representing the mechanical property of the biological tissue at a plurality of depths including the depth location of the tissue layer and depths outside the depth location of the tissue layer;

mapping the 2D distributions into a 3D data set representing the distributions of the viscoelastic parameter in relation to the plurality of depths that indicates a 3D distribution of stiffness of the tissue at the depth location of the tissue layer and depths outside the depth location of the tissue layer; and wherein said calculating includes calculating 2D distributions of a frequency-dependent viscoelastic parameter.

25. A method according to claim 24, further comprising performing interferometric coherence-gating of light detected with the optical detector.

26. A method according to claim 24, wherein the 3D distribution of stiffness of the tissue relates to an extra-cellular matrix (ECM) at the depth location of the tissue layer and depths outside the depth location of the tissue layer.

27. A method according to claim 26, further comprising at least one of (i) color-coding a calculated 2D distribution of the viscoelastic parameter depending at least in part on a value of said viscoelastic parameter, and (ii) displaying a visual representation of at least one of said color-coded 2D distribution and said 3D data set showing the stiffness of the extra-cellular matrix (ECM).

28. A method according to claim 24, further comprising forming an optical interferogram by overlapping a sample distribution of light that has been transmitted to the biological tissue through a sample train of optical components and has interacted with a tissue layer, and a reference distribution of light, which has passed through a reference train of optical components including an optical delay line with a variable optical delay length, wherein the sample and reference distributions of light are coherent.

29. A method according to claim 28, further comprising reconstructing said interferogram in a computer process to form a spatially-filtered optical interferogram.

30. A method according to claim 28, wherein said depth of the biological tissue layer is defined by an optical distance between the biological tissue and an element of at least one of the sample and reference trains of optical components.

31. A method according to claim 30, further comprising changing the optical distance by an incremental amount not exceeding the coherence length.

32. A method according to claim 31, wherein said changing includes repositioning of an optical component of the sample train and adjusting a variable optical delay length by an amount optically matching said incremental amount.

33. A method according to claim 24, wherein said calculating includes calculating 2D distributions from optical data that represents Brownian motion displacements of intrinsic light-scattering particles of the biological tissue.

* * * * *